United States Patent [19]

Jenkins

[11] 4,265,240

[45] May 5, 1981

[54] APPARATUS FOR PROVIDING A CONTROLLED INTRODUCTION OF INTRAVENOUS FLUID TO A PATIENT

[75] Inventor: Jon A. Jenkins, Rancho Santa Fe, Calif.

[73] Assignee: IMED Corporation, San Diego, Calif.

[21] Appl. No.: 30,161

[22] Filed: Apr. 16, 1979

[51] Int. Cl.³ .............................................. A61M 5/00
[52] U.S. Cl. ........................ 128/214 E; 128/DIG. 12
[58] Field of Search ........... 128/214 E, 214 F, 214 R, 128/214 C, DIG. 12, DIG. 13, 260

[56] References Cited

U.S. PATENT DOCUMENTS

| | | | |
|---|---|---|---|
| 3,749,285 | 7/1973 | Latham, Jr. ................. | 128/DIG. 13 |
| 4,094,318 | 6/1978 | Burke et al. ..................... | 128/214 E |
| 4,105,028 | 8/1978 | Sadlier et al. ..................... | 128/214 E |
| 4,111,198 | 9/1978 | Marx et al. ....................... | 128/214 E |
| 4,114,144 | 9/1978 | Hyman ............................. | 128/214 E |

Primary Examiner—John D. Yasko
Attorney, Agent, or Firm—Ellsworth R. Roston; Charles H. Schwartz

[57] ABSTRACT

First and second means respectively provide for a passage of first and second particular volumes of fluid from first and second sources at first and second controlled rates to a patient. Each of the first and second means is constructed to provide on a positive basis for the flow of fluid at the particular one of the first and second controlled rates. Third means are operatively coupled to the first and second means for providing for an initial operation of the first means in producing a passage of fluid from the first source to the patient. Fourth means are responsive to the passage of the first particular volume of fluid to the patient for interrupting the operation of the first means and instituting the operation of the second means in providing for the passage of fluid from the second source to the patient.

The passage of fluid from the first means to the patient is also interrupted when all of the fluid has passed from the source. At such a time, an air sensor associated with microbore tubing indicates that fluid is no longer passing through the tubing. At such a time, however, a drip chamber receiving the fluid from the microbore tubing still has fluid because the volume of the drip chamber is greater than the volume of the microbore tubing. Since the fluid from the drip chamber is introduced to the first means for passage on a controlled basis to the patient, the air sensor becomes operative to interrupt the flow of fluid to the patient at a time when air bubbles cannot flow to the patient. The drip chamber is made from a resilient material so that it can be initially operated to squeeze into the source any air bubbles existing in the drip chamber before fluid starts to pass from the first source to the patient.

13 Claims, 3 Drawing Figures

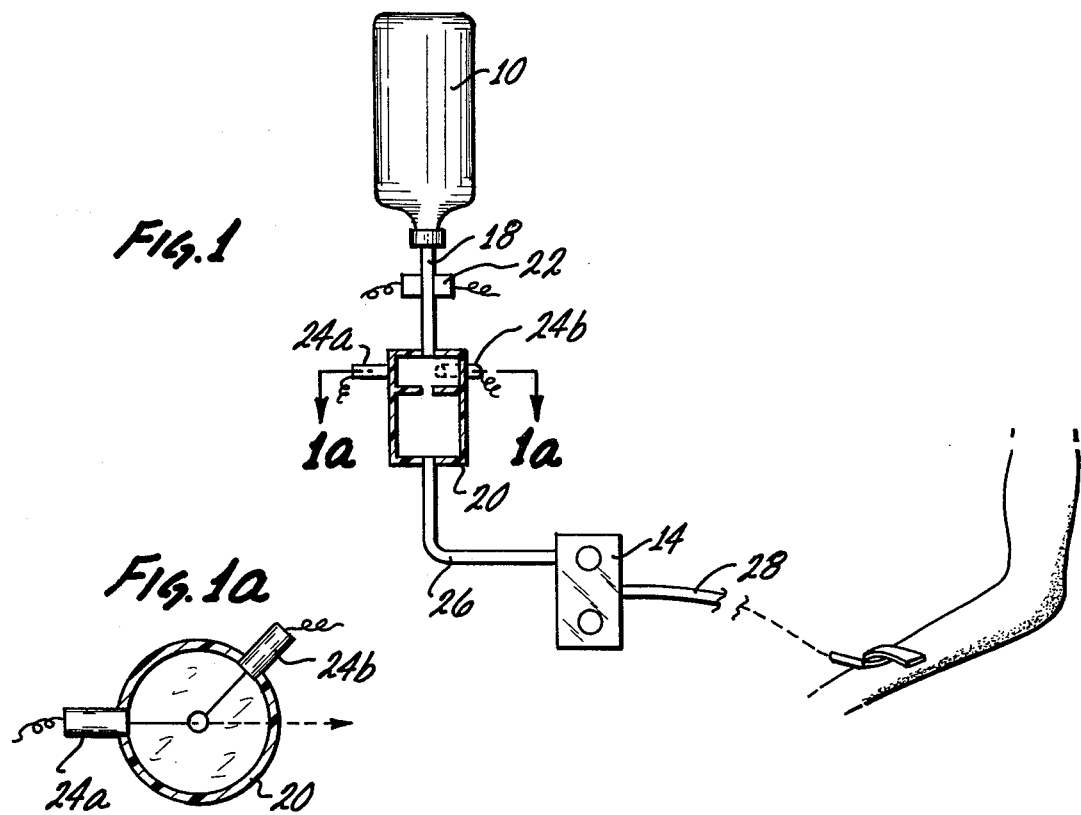
Fig.1
Fig.1a
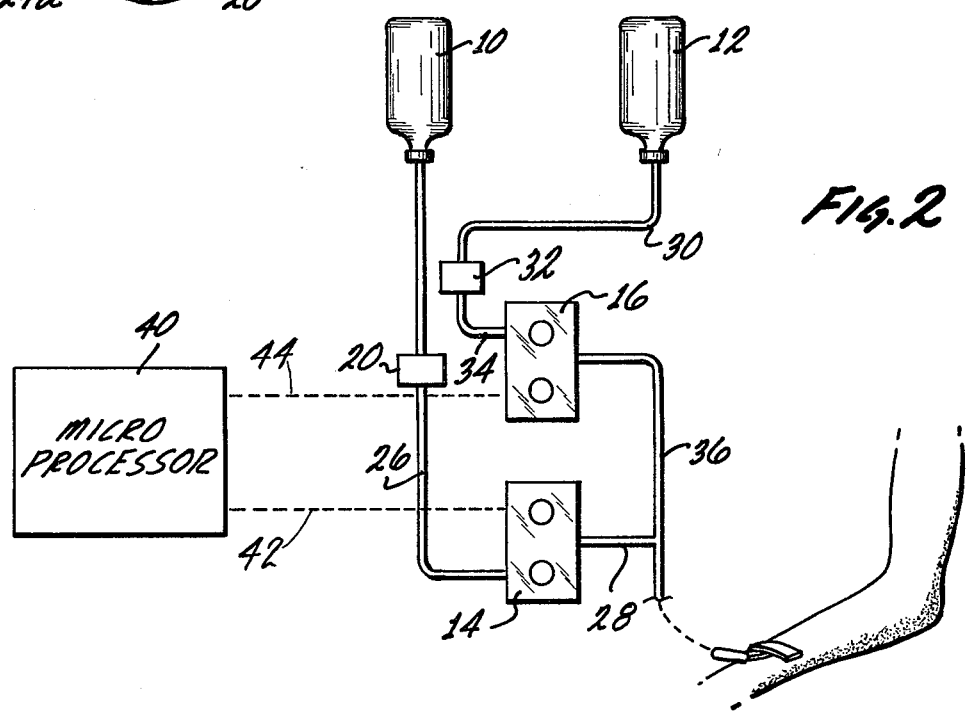
Fig.2

APPARATUS FOR PROVIDING A CONTROLLED INTRODUCTION OF INTRAVENOUS FLUID TO A PATIENT

This invention relates to a system for controlling the sequential passages of fluid to a patient from different sources at individually controlled rates. The invention also relates to a system for insuring that the passage of fluid to the patient from each individual source is interrupted after the passage of all of the fluid from the source but before the passage of any air bubbles to the patient.

As medical knowledge advances, the treatment of patients has become increasingly complex. For example, after an operation, a patient often receives antibiotics at a controlled rate to minimize the possibility of infections. The patient may thereafter receive a solution of dextrose to provide the patient with a source of energy and to maintain a balance of fluid in the body or the patient may receive a saline solution to maintain this balance of fluid in the body.

The introduction of successive solutions into a patient's body has created hardships on the nursing corps in a hospital, particularly at a time when a shortage of nurses appears to have developed in many hospitals. For example, the nurses have had to maintain a watch over the passage of the first fluidic solution such as the antibiotic solution to the patient to insure that all of this fluid passes to the patient without the passage of any air bubbles after the passage of the antibiotic solution. The nurses have then had to disconnect the antibiotic solution and to connect the second solution such as the dextrose solution or the saline solution so that this solution then passes to the patient. As will be seen, such procedures have been crude at best.

The crude methods described in the previous passage have created unique problems regardless of the alternatives that have been followed. As one alternative, the nurses have had to exercise special and continuing care to disconnect the first source from the patient at the proper moment. In this alternative, the nurses have had to check frequently and have accordingly lost valuable time from their other duties. As a second alternative, the nurses have not checked as frequently with attendant increases in the possibility that the first source has not become disconnected from the patient until all of the fluid has flowed from the source and the risk of an air bubble passing to the patient. As will be seen, neither alternative is completely welcome.

Other problems have also existed in the methods and apparatus available for introducing venous fluid to a patient. For example, problems have existed in detecting when the fluid flowing from a source to a patient becomes exhausted. The problem has existed because air has tended to flow to the patient during arterial and subclavian infusions when the fluid from the source has become exhausted. The flow of air to a patient is dangerous because it blocks the circulation of blood through the venous system and tends to produce heart failure in the patient.

Various attempts have been made to solve the problems discussed above but such attempts have not been entirely successful. For example, in spite of such efforts, nurses still have to monitor the flow of fluid to a patient and have to manually shift from one source to another when the fluid from the first source has become exhausted. Furthermore, the systems now in use tend to detect air in a flow line only when all of the fluid from a source has flowed through a line to a patient. This is sometimes too late because the sensing occurs after air has flowed into the line and through the line to the patient.

This invention provides a system which overcomes the above disadvantages. The invention includes a first pump or controller and a second pump or controller. The sysetm is not exclusive in that a pump can constitute one of such means providing a flow of fluid and a controller can constitute the other one of such flow-producing means. The first and second flow-producing means are respectively connected at their inputs to first and second sources of fluid and are connected at their outputs to the patients. The system is constructed to provide initially for a flow of fluid from the first flow-producing means until such time as all of the fluid has flowed from the first source to the patient. The system is then operative to decouple the first source and the first flow-producing means from the patient and simultaneously to couple the second source and the second flow-producing means to the patient.

In this way, a system with flexible capabilities can be provided where the first and second fluids can have individual characteristics and where the fluids can flow in a particular sequence to the patient. Although only first and second sources of fluid and first and second flow-producing means are disclosed, a plurality of such arrangements can be sequentially provided to introduce a plurality of different fluid solutions in sequence to a patient.

The system of this invention also includes other advantageous features. For example, a drip chamber may be provided in the system between each source and its associated flow-producing means. The drip chamber may be made from a suitable material having properties of being squeezable and of returning to its original shape after being squeezed. Tubing with a small opening such as a microbore opening having an inner diameter on the order of fifty thousandths inch (0.050″) may be connected between each source and the associated flow-producing means. A sensor may be disposed adjacent the microbore tubing to provide an indication when air flows through the tubing.

By providing a drop chamber and microbore tubing, the volume of the fluid in the drip chamber exceeds the volume of the fluid in the tubing. By providing such an arrangement and by making the drip chamber from a squeezable material, the drip chamber may be initially squeezed to displace air into the source to a position above the liquid in the source. The liquid in the source then flows to the patient without any initial flow of air to the patient. When all of the liquid flows from the source and the microbore tubing, the sensor is energized to deactivate the flow-producing means. At this time, liquid still remains in the drip chamber because the drip chamber has a larger volume than the microbore tubing. In this way, the flow of fluid to the patient is interrupted before air can flow to the patient. The system accordingly operates on a fail-safe basis to insure the safety of the patient.

In the drawings:

FIG. 1 is a schematic view of a system for insuring that the flow of each fluid is interrupted before any air can flow to the patient;

FIG. 1a is a sectional view taken substantially on the line 1a—1a of FIG. 1 and shows further details of construction of a drip chamber and air sensor included in the embodiment shown in FIG. 1; and FIG. 2 is a schematic view of a system constituting one embodiment of the invention for producing in sequence the flows of different fluids to a patient.

In the embodiment shown in the drawings, a pair of sources 10 and 12 of fluid may be provided. The fluid in the source 10 may be different from the fluid in the source 12. For example, the fluid in the source 10 may constitute an antibiotic solution and the fluid in the source 12 may constitute a dextrose or saline solution, possibly with an electrolyte like potassium chloride. Although two sources 10 and 12 are shown, other sources may also be included.

A pair of flow-producing means are respectively associated with the sources 10 and 12. Each of the flow-producing means may constitute a pump or a controller. A suitable pump is disclosed and claimed in my U.S. Pat. No. 3,985,133 issued to me on Oct. 12, 1976, for an IV PUMP, and assigned of record to the assignee of record of this application. A suitable controller is disclosed and claimed in application Ser. No. 913,294 filed by me on June 7, 1978, for "System for Controlling the Flow of Intravenous Fluids to a Patient" and assigned of record to the assignee of record of this application. The use of pumps or controllers is not exclusive. In other words, on of the flow-producing means may constitute a pump and the other may constitute a controller. For convenience, the flow-producing means are designated as pumps 14 and 16.

Suitable tubing 18 such as microbore tubing extends from the source 10 to a drip chamber 20. When microbore tubing is used, the tubing may have a small axial opening with a suitably small diameter such as approximately fifty thousandths of an inch (0.050") and a suitable length such as approximately twenty-six inches (26"). A drop sensor 22 having a conventional construction is disposed adjacent the microbore tubing to sense the drops of fluid flowing from the source 10 to the drip chamber 20.

The drip chamber 20 may be made from a suitable material, such as a plastic, which can be squeezed. The drip chamber is also provided with resilient characteristics so that it will return to its original condition when it is released after being squeezed. The volume of the drip chamber exceeds the volume of the bore in the tubing 18. For example, the drip chamber may have a volume of approximately five (5) cubic centimeters.

An air sensor 24 having a conventional construction is operatively associated with the drip chamber 22 at a position near the top of the drip chamber. The air sensor 24 is connected to the pump 14 to obtain an interruption in the operation of the pump when it senses air at the top of the drip chamber. The drop sensor 24 may include a light source 24a and a photocell 24b.

A tube 26 is connected between the bottom of the drip chamber and the pump 14. A tube 28 extends between the pump 14 and the patient. The tubes 26 and 28 may have inner bores greater than the microbore of the tubing 18.

Microbore tubing 30 and a drip chamber 32 may be connected between the source 12 and the pump 16 in a manner similar to that described above for the tubing 18 and the chamber 22. Tubes 34 and 36 corresponding to the tubes 26 and 28 may provide for a flow of fluid from the drip chamber 32 through the pump 16 to the patient.

A microprocessor 40 may be associated with the pump 14 to process the information represented by the fluid flowing through the pump and to produce signals in accordance with this processed information. A line 42 extends from the microprocessor 40 to the pump 14. A line 44 extends from the microprocessor 40 to the pump 16. The lines 42 and 44 are shown schematically by broken lines.

Before the apparatus constituting this invention is placed in operation, the drip chamber 20 is squeezed. This causes the air in the drip chamber 20 and in the microbore tubing 18 to be directed upwardly into the source 10. The air rises through the liquid in the source 10 to a position above the liquid. When the drip chamber 20 is released, liquid in the source 10 flows through the microbore tubing 18 into the drip chamber 20. In this way, only liquid appears in the microbore tubing 18 and the drip chamber 20. This prevents air from passing to the patient. The air in the drip chamber 32 is replaced by liquid from the source 12 in a similar manner. The apparatus constituting this invention then becomes operative. Liquid from the source 10 is initially pumped by the pump 14 to the patient. The flow of the liquid to the patient occurs at a controlled rate dependent upon the setting of the pump 14. The pump 14 is also operative to count the volume of the liquid passing through the pump to the patient. When the volume of such liquid reaches a particular level, the microprocessor 40 produces a signal which is introduced to the pump 14 to discontinue the operation of the pump and is introduced to the pump 16 to produce an operation of this pump. The volume of liquid preset into the microprocessor 40 preferably is slightly less than the liquid in the source 10.

When the pump 16 becomes operative, it provides for a flow of liquid from the source 12 to the patient. This flow is at a rate dependent upon the setting of the pump 16. For example, the flow of liquid from the pump 16 may be at a relatively low rate compared to the flow from the pump 14, particularly when the flow is primarily to maintain the line to the patient open. The flow of the fluid from source 10 to the patient continues until a particular volume dependent upon the setting of the microprocessor 40 has been reached.

The apparatus constituting this invention is also operative to assure in other ways that air cannot flow to the patient. For example, if all of the liquid flows from the source 10 and the microbore tubing 18, the air sensor 24 becomes operative to provide for an interruption in the operation of the pump 14. At such a time, liquid still remains in the drip chamber 20. This assures that air cannot pass to the patient even when all of the liquid in the source 10 has been exhausted.

The apparatus accordingly provides for a sequential flow of fluids to a patient at individual rates from at least two different sources, each containing a unique solution. The apparatus further assures that air cannot flow to a patient at any time from the beginning to the end of such a flow sequence.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination for providing for the flow of fluid to a patient, first means for providing for a passage of a first particular volume of fluid at a first controlled rate to the patient, second means for providing for a passage of a second particular volume of fluid at a second controlled rate to the patient where the second particular rate is different from the first particular rate, third means operatively coupled to the first and second means for providing for an initial operation of the first means in producing a passage of fluid to the patient, fourth means responsive to the passage of the first particular volume of fluid to the patient for interrupting the operation of the first means and instituting the operation of the second means, a first source of fluid, a drip chamber, first hollow tubing extending from the first source to the first tubing and having a volume less than that of the drip chamber, second hollow tubing extending from the drip chamber to the first means, and sensor means associated with the first hollow tubing at a position adjacent the drip chamber for sensing when the fluid from the first source no longer flows through the first hollow tubing.

2. The combination set forth in claim 1, including, means associated with the first means for insuring that air bubbles do not flow to the patient when the operation of the first means becomes discontinued.

3. In combination for providing for a controlled flow of fluid to a patient, a source of a particular volume of the fluid, first means for providing for a controlled flow of fluid to the patient at a particular rate, means for storing a limited amount of the fluid from the source, first conduit means having a volume less than that of the storing means and extending from the source to the storing means, second conduit means extending from the storing means to the first means for providing for the passage of the fluid from the storing means to the first means, third conduit means extending from the first means to the patient for providing for the passage of the fluid from the first means to the patient, and sensing means operatively associated with the first conduit means at a position adjacent the storing means for sensing when fluid no longer flows from the source to the storing means.

4. The combination set forth in claim 3 wherein the first conduit means constitutes a microbore tubing of a length providing a volume of fluid storage less than the volume of the storing means.

5. The combination set forth in claim 4 wherein the storing means constitutes a drip chamber made from a resilient material having properties of being squeezed to eliminate air within the chamber and having properties of returning to its initial form after being squeezed.

6. The combination set forth in claim 5 wherein second sensor means are operatively coupled to the first sensor means for sensing the periodic flow of drops through the first hollow tubing.

7. In combination for providing for a controlled flow of fluid to a patient, first means for providing for a passage of a first particular volume of fluid at a first controlled rate to the patient, second means for providing for a passage of a second particular volume of fluid at a second controlled rate to the patient, a first source of fluid, a second source of fluid, third means for providing for the introduction of fluid from the first source to the first means, fourth means for providing for the introduction of fluid from the second source to the second means, fifth means for providing for an introduction of fluid from the first means and the second means to the patient, means operatively coupled to the first means and the second means for initially providing for an operation of the first means until the passage of the first particular volume of fluid through the first means to the patient and for thereafter discontinuing the operation of the first means and for providing for an operation of the second means, the third means including first resilient means for storing a particular amount of fluid and having properties of initially being squeezed to eliminate air from the resilient means and provide a substitution of liquid from the first source, and and fourth means including second resilient means for storing a particular amount of fluid and having properties of initially being squeezed to eliminate air from the resilient means and provide a substitution of liquid from the second source.

8. The combination set forth in claim 7, including, means responsive to the flow of air through the third means for discontinuing the operation of the first means, and means operatively associated with the third means for initially providing for the exhaustion of air from the third means before the operation of the first means is initiated.

9. The combination set forth in claim 7, including, the third means including first microbore tubing having an internal volume less than the volume of the first resilient means and disposed between the first source and the first resilient means, and the fourth means including second microbore tubing having an internal volume less than the volume of the second resilient means and disposed between the second resilient means.

10. In combination for providing for a controlled flow of fluid to a patient, a source of a particular volume of fluid, first means having squeezable properties for storing a particular amount of liquid from the source and for eliminating air when squeezed, first tubing extending from the source to the first means and having an internal volume less than the volume of the first means, second means for providing a controlled flow of fluid at a particular rate, second tubing extending from the first means to the second means to provide for the flow of fluid from the first means in accordance with the operation of the second means, and means associated with the first means for sensing the presence of air to obtain an interruption in the operation of the second means.

11. The combination set forth in claim 10, wherein, the first means includes a drip chamber made from a material having properties of being squeezed and of returning to its original form after being squeezed and the first tubing has a microbore opening.

12. The combination set forth in claim 10, including, a second source corresponding to the first source, third and fourth tubing respectively corresponding to the first and second tubing, third means respectively corresponding to the first means, fourth means for providing a controlled flow of fluid at a particular rate, second sensing means corresponding to the first sensing means, and means operatively coupled to the second and fourth means for initially providing an operation of the second means and for interrupting the operation of the second means and initiating the operation of the fourth means after the flow of a particular amount of fluid from the first source.

13. The combination set forth in claim 12, wherein, each of the first and third means includes a drip chamber made from a material having properties of being squeezed and of returning to its original form after being squeezed, and the first and third tubings having microbore openings.

* * * * *